United States Patent [19]

Blake

[11] Patent Number: 4,573,979
[45] Date of Patent: Mar. 4, 1986

[54] IRRIGATION/ASPIRATION TIP
[75] Inventor: Larry W. Blake, Irvine, Calif.
[73] Assignee: Innovative Surgical Products, Inc., Santa Ana, Calif.
[21] Appl. No.: 644,057
[22] Filed: Aug. 23, 1984
[51] Int. Cl.$^4$ ............................................. A61M 5/325
[52] U.S. Cl. ................................... 604/240; 604/275; 604/35
[58] Field of Search ............... 604/240, 275, 280, 283, 604/27, 35, 43, 264

[56] References Cited
U.S. PATENT DOCUMENTS

| | | | |
|---|---|---|---|
| 3,439,675 | 4/1969 | Cohen | 604/275 |
| 3,884,231 | 5/1975 | Peters | 604/275 |
| 3,906,954 | 9/1975 | Baehr et al. | 604/27 |
| 3,968,796 | 7/1976 | Baker | 604/35 |
| 4,397,640 | 8/1983 | Haug et al. | 604/35 |
| 4,402,684 | 9/1983 | Jessup | 604/43 |

Primary Examiner—John D. Yasko
Attorney, Agent, or Firm—Knobbe, Martens, Olson & Bear

[57] ABSTRACT

In an irrigation/aspiration, surgical instrument for intraocular eye surgery, an inner cannula provides aspiration while a larger, but coaxially-spaced outer cannula provides irrigation. The outer cannula is made of metal but is connected to the tip of the surgical instrument by a flexible, silicon rubber support so that the outer cannula is relatively flexible compared to the stiffness of the cannula. Thus the outer cannula can be rotated or repositioned without distortion since all of the motion is localized at the flexible support.

15 Claims, 5 Drawing Figures

IRRIGATION/ASPIRATION TIP

BACKGROUND OF THE INVENTION

This invention relates to the field of intraocular surgery, and in particular to surgical instruments used to irrigate and simultaneously aspirate body fluids during intraocular surgery.

In eye surgery, the need often arises to remove fluids from the eye or to break up and remove tissue or material from the eye. For example, the need for such removal of material and fluids commonly arises during lensectomies wherein the lens of the eye is removed and replaced. Various techniques have been developed whereby needles or cannula can be inserted into various portions of eye in order to break up or remove these bodily tissues and fluids.

Several methods of breaking up and removing ocular materials require the insertion or addition of fluids to irrigate the surrounding portions of the eye. The fluid is then aspirated, usually simultaneously with the irrigation, to remove the materials which had been loosened and are entrained within the irrigation fluid. This simultaneous irrigation/aspiration operation can be achieved by using two coaxial cannula with the inner cannula providing the aspiration while the outer cannula provides the irrigation, or vice vera.

The inner and outer cannula essentially form a tube within a tube with a very small space in between the two tubes. This small space between tubes makes it difficult to surgically sterilize the instruments after they have been used.

The sterilization problems are minimized by using a disposable outer cannula which is removed and discarded after use so that the inner cannula can be sterilized and reused. The disposable outer cannula is often made of a flexible elastomeric material such as silicon. The thin silicon cannula can be integrally molded to a silicon base which slips over the tip of the surgical instrument supporting the inner cannula. The flexible silicone forms an effective leak proof seal to insure predictable fluid flow during irrigation.

A silicone cannula and support structure has the advantage of being relatively inexpensive, but more importantly, the cannula can bend freely. Surgeons sometimes bend the inner and outer cannulas to facilitate access to various portions of the eye, as when the surgeon must reach over the bridge of the nose to reach the medial portions of the eye. The inner cannula is usually thin enough to bend without buckling or crimping. A silicone outer cannula can freely bend without permanently buckling, although buckling and flow restriction do occur.

A flexible, outer silicone cannula also makes it easy to change the spacing between the irrigation and aspiration apertures when the cannulas are bent. The distance between the aspiration aperture and the irrigation apertures can be varied by screwing the inner cannula inward or outward. This screw extension and retraction requires the cannulas to rotate. When the inner cannula is bent, then in order to rotate, the inner cannula must bend or rotate the outer cannula. Since the outer cannula is fastened to the tip of the surgical instrument, it cannot rotate. A rubber outer cannula can be freely bent by the inner cannula to allow the rotational extension or retraction. A metal outer cannula is not bent so easily, and may be too stiff to be bent by the inner cannula. Repeated bending of the outer metal cannula also raises the risk of metal fatigue and fracture.

A flexible, outer silicone cannula also makes it easy to rebend and re-orient the cannulas. Some surgical irrigation/aspiration instruments allow the inner cannula to be rotated. Once the inner cannula is bent, rotating of the inner cannula to facilitate repositioning by the surgeon is hindered unless the outer cannula can freely rotate. Metal outer cannulas usually inhibit rotational adjustment when they are bent since the inner cannula is often not strong enough to bend the outer cannula as the inner cannula is rotated. Silicone outer cannulas do not inhibit this rotational adjustment since the rubber freely bends.

The silicone rubber outer cannula is not without its problems, however. The rubber cannot be molded as thin as metal. Thus rubber cannulas require larger incisions in order to be inserted into the eye. Also, the rubber is not as smooth as metal, which can create problems in obtaining a smooth, clog free fluid flow, and can possibly tear the soft tissue sliding along the length of the rubber cannula. Further, the rubber does not buckle during bending so as to restrict fluid flow. On occasion, the rubber outer cannula has buckled or axially collapsed during insertion into the eye with the result that the collapsed rubber tears the eye since it is too large and rought to fit smoothly through the incision in the eye. The buckling collapse is especially prone to occur at the tip of the outer cannula where the irrigation apertures are located.

Many surgeons also prefer a more rigid material than the soft silicon rubber since it is occasionally necessary to suture the sclera or other portions of the eye around the outer cannula with the result that a suture can radially compress the soft silicon cannula and cut off fluid flow through the outer cannula. Using a metal outer cannula overcomes the concern that the sutures may restrict the flow between the inner and outer cannula. Unfortunately, making the outer cannula out of surgically compatible metal is expensive. Additionally, the common way of fastening a metal outer cannula and its metal base to the surgical instrument is by threading the base portion of the outer cannula. This threading operation contributes to the increased cost of the outer cannula.

Using an outer cannula and support base made entirely of metal also presents problems when the inner and outer cannulas are bent by the surgeon in order to facilitate surgical access to various portions of the eye. Bending the cannula usually buckles and crimps the outer cannula and restricts the fluid flow, especially the fluid flow between the inner and outer cannula. Repeated bending of the inner and outer cannula can result in fatigue and fracture of the metal outer cannula. The outer cannula usually fatigues and fractures before the inner cannula since it is of larger diameter and thus is inherently less flexible than the thinner inner cannula.

There have been recent attempts to commercially produce a surgical instrument containing a metal inner and outer cannula wherein the entire surgical instrument is disposable. Making the entire instrument disposable is not only more expensive, but results in the waste of a significant amount of materials compared to only disposing the outer cannula and its support base.

There is thus a need for a lightweight, disposable outer cannula which has sufficient radial stiffness to allow suturing around the cannula without restricting the fluid flow, yet which can allow the outer cannula to be bent with minimum obstruction to the fluid flow between the inner and outer cannula. This cannula must be inexpensive to make yet still form an effective, leak proof seal when attached to the surgical instrument.

SUMMARY OF THE INVENTION

Summarily described, an outer, radially stiff cannula is mounted to a flexible support structure to provide a flexible, yet lightweight and disposable unit.

In a surgical instrument used for simultaneous irrigation and aspiration during ocular surgery, there is an inner cannula containing an aspiration aperture adjacent the external end or tip of the cannula. The aperture is used for aspiration of ocular fluids and materials. An outer cannula surrounds the inner cannula but its length does not generally extend beyond the aspiration aperture in the inner cannula. An irrigation aperture adjacent the external end of the outer cannula is used to irrigate the eye. Both the inner and outer cannula are mounted on a surgical instrument which provides irrigation fluid to the space between the inner cannula and the outer cannula, the instrument further aspirates the ocular fluid and materials through the inner cannula.

The outer cannula is made of a stiff or rigid material such as metal or hard plastic. The use of a rigid outer cannula prevents any restriction of fluid flow when sutures are tightened around the radially stiff, outer cannula. The use of such strong materials such as metal for the outer cannula also reduces the outer diameter of the cannula, thus, minimizing the size of the surgical incision needed to insert the cannula into the eye. A metal outer cannula is also smooth so as to minimize abrasion damage to any eye tissue rubbing against the cannula.

The stiff outer cannula is connected to a flexible support structure made of a flexible elastomer such as silicone. The use of a soft and flexible silicon on the base of the cannula allows the outer cannula to flex with the inner cannula with minimum reduction of fluid flow between the inner and outer cannulas. The flexible support structure prevents buckling or crimping of the cannula as would reduce fluid flow, or as would induce fatigue and fracture of the cannula. The flexible support structure allows free rotation of the inner cannula to vary the spacing between the irrigation and aspiration apertures, or to allow repositioning of the cannulas.

The end of the flexible support structure adjacent the juncture with the end of the rigid outer stiff cannula is shaped to provide a support which allows some axial flexibility to the outer cannula. Thus, if the end of the outer cannula contacts some of the soft eye tissue during insertion of the surgical instrument, the outer cannula has some axial give or flexibility in order to minimize inadvertent damage to the eye tissue during insertion.

The flexible silicon support structure attaches to the lower portion of the cannula adjacent the surgical instrument so as to provide an inexpensive, yet effective seal which can be quickly installed or removed from the surgical instrument. The flexible silicon support structure can be molded with internal threads so it can be screwed onto the end of the surgical instrument, or alternatively, the silicon is flexible enough that it can be stretched over the end of the surgical instrument to form an effective seal which will not hinder the performance of the irrigation/aspiration instrument.

DESCRIPTION OF THE DETAILED DRAWINGS

The foregoing features and advantages of the invention are explained in greater detail in the preferred embodiment and in the description of the accompanying drawings, in which.

DESCRIPTION OF THE PREFERRED EMBODIMENT

Figure 1:
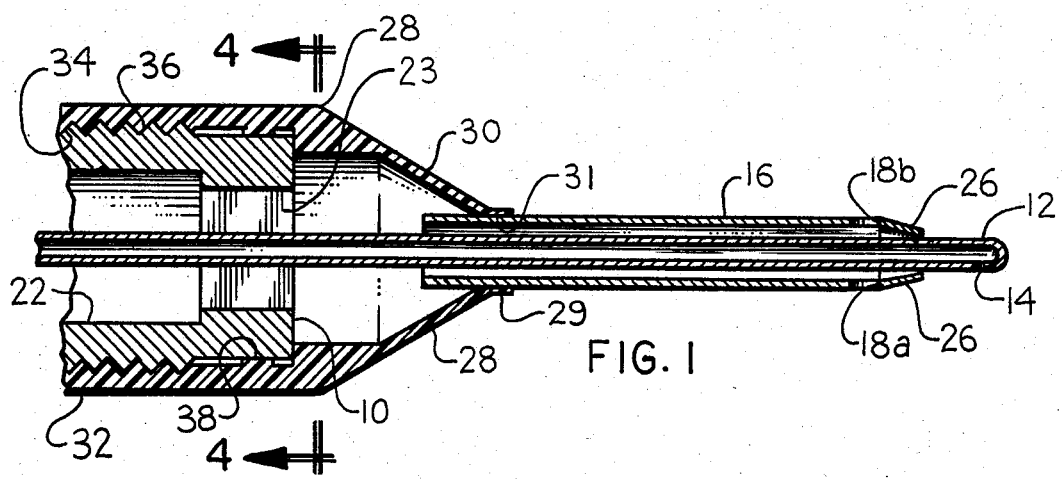
FIG. 1 is a sectioned, side elevational view showing the inner and outer cannulas of this invention.

Briefly described, FIG. 1 shows the tip of a surgical instrument 10 which is used to simultaneously irrigate and aspirate the eye during ocular surgery such as a lensectomy. The irrigation/aspiration surgical instrument 10 functions by exerting a controlled vacuum on a needle or inner cannula 12 so that ocular fluid or materials can be aspirated through an aspiration aperture 14 in the tip of the inner cannula 12 when the cannula 12 is inserted into an eye. An irrigation sleeve or outer cannula 16 is concentric with and surrounds most of the inner cannula 12, but there is an annular space between the inner cannula 12 and the outer cannula 16. Diverse irrigating fluids such as saline solution or distilled water can be forced under pressure through this annular space between the inner cannula 12 and the outer cannula 16. The pressure irrigation devices are well known in the art and are not described in detail herein. The irrigating fluid exits through irrigation apertures 18a and b which are adjacent the end of the outer cannula 16. Thus, the outer cannula 16 provides for irrigation of the eye while inner cannula 12 provides for simultaneous aspiration. The relative rates of irrigation and aspiration can be independently varied and controlled.

Referring to FIG. 1, the inner cannula 12 is a thin, needle-like, tubular member which extends from the tip of the surgical instrument 10. The external end of the inner cannula 12 is blocked but there is an aspiration aperture 14, radially oriented, which is located adjacent the external end of inner cannula 12. The inner cannula 12 is of sufficiently small diameter, and has sufficiently thin cylindrical walls, such that it can be bent without buckling or crimping as would lead to low cycle fatigue fracture of the inner cannula 12. The inner cannula 12 is typically, and preferably, made of a surgically compatible metal.

The inner cannula 12 communicates with a vacuum or suction device which is well known in the art and is not described in detail herein. The result is that fluids and entrained materials can be sucked through the aspiration aperture 14 in inner cannula 12 in order to remove those fluids and materials from the eye.

Figure 4:
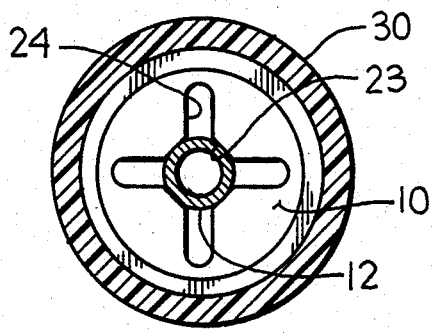
FIG. 4 is a sectional view taken along 4—4 of FIG.
Figure 5:
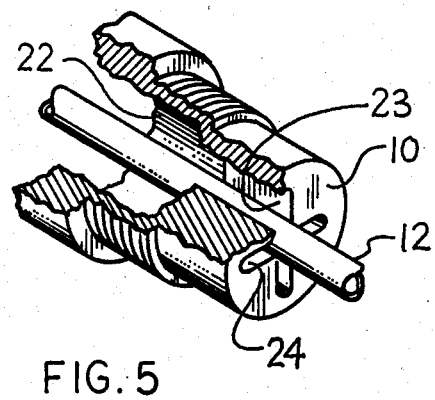
FIG. 5 is a partially sectioned perspective view of the tip of the surgical instrument and the cannula.

As shown in FIGS. 1, 4 and 5, and especially in FIG. 5, the tip of surgical instrument 10 contains plural, radially inward projections 23 forming apertures or slots 24, which slots open into a cylindrical aperture 22. the projections 23 radially support and position the inner cannula 12. As shown in FIGS. 4 and 5, there are four radial slots 24 oriented along two axes which are mutually perpendicular to one another so as to form an X or cross configuration. The inner cannula 12 extends through the center or crossing points of the slots 24.

Referring to FIGS. 1 and 5, there is an internal, central cylindrical aperture 22 in the surgical instrument 10, through which the inner cannula 12 passes. Plural slots 24 communicate with cylindrical aperture 22, which in turn communicates with a pressurized irrigation apparatus (not shown) to provide a pressurized irrigating fluid which passes through cylindrical aperture 22 along the outside of the inner cannula 12. The irrigating fluid exits the tip of surgical instrument 10 through the slots 24.

Figure 2:
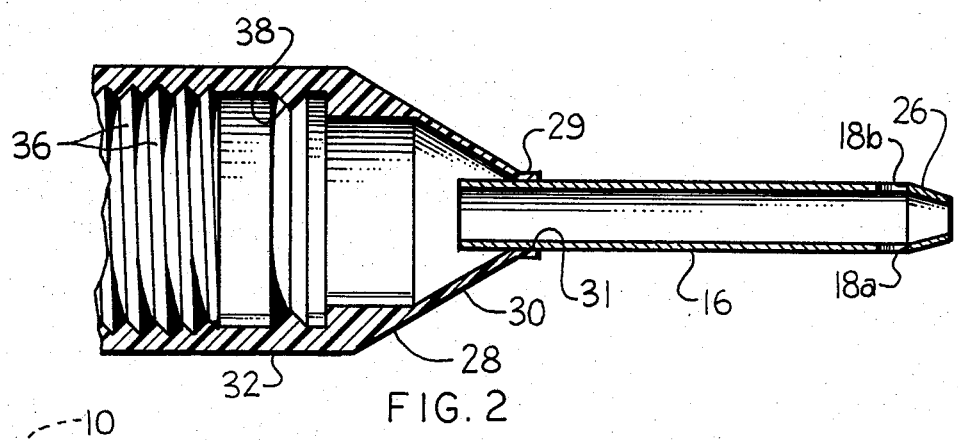
FIG. 2 is a sectioned side elevational view showing the outer metal cannula and the flexible support structure of this invention.

FIGS. 1 and 2 shown the irrigation sleeve, or outer cannula 16 which is coaxial with, and substantially surrounding the inner cannula 12. The outer cannula 16 is a short cylindrical segment having relatively thin walls so as to form a tube or cannula. The inner diameter of the outer cannula 16 is larger than the outer diameter of the inner cannula 12 so that there is an annular space between the inner cannula 12 and the outer cannula 16.

The external end of outer cannula 16 terminates adjacent the aspiration aperture 14 in the inner cannula 12. Adjacent the external end 25 of the outer cannula 16 are two irrigation apertures 18a and b. The external end 26 of outer cannula 16 tapers radially inward so as to end immediately adjacent to the inner cannula 12 (FIG. 1). The irrigation apertures 18 are often placed on this tapered section. The external end 26 of outer cannula 16 is sufficiently close to the inner cannula 12 so that very little irrigation fluid escapes from the gap between the external end 26 and the inner cannula 12. A gap of a few thousandths of an inch will work, while a gap of about one to two thousandths of an inch is preferable. The outer cannula 16 can be made of any stiff material which is surgically compatible, such as metal or hard plastic, but preferably metal. A typical outer cannula 16 is of 16 gage metal, with an outer diameter of 0.0650±0.0005 inches, and an inner diameter of 0.060 inches ±0.001 inches.

The end of outer cannula 16 which is adjacent the tip of the surgical tool 10 when in use, is connected to a support structure 28. The support structure 28 has a tapering or conical section 30 which tapers to a cylindrical portion 29 which forms a cylindrical aperture 31 into which the end of outer cannula 16 is inserted and bonded. An included conical half angle of sixty (60) degrees has been found suitable. The support structure 28 is made of a flexible, surgically compatible, elastomeric material such as silicone rubber. A silicone rubber having a 55 shore A hardness has been found suitable, with the thickness of conical section 30 being about 0.030 inches.

The metal outer cannula 16 is bonded to the flexible silicone support structure 28 by sandblasting the end of the outer cannula 16 to increase the bonding area and bonding efficiency. A primer, is then applied to the sandblasted area to facilitate bonding to the metal outer cannula 16.

The primer creates a bonding surface compatible with both a metal and silicone. Such a primer is commercially available from Hughson Chemicals, Lord Corporation, Erie, Pa., under the name Chemlok®, manufacturer's designation being AP132. A commercially available adhesive, such as GE 118, is then applied to the primed end of the outer cannula 16. The primed end of outer cannula 16 is then inserted into and bonded to the cylindrical aperture 31 in the flexible support structure 28.

As shown in FIGS. 1 and 2, the end of the outer cannula 16 is inserted into the cylindrical aperture 31 so that is ends substantially adjacent end of the cylindrical portion 29. Alternately phrased, the outer cannula 16 does not substantially extend into the conical cavity formed by the conical section 30. If the end of the outer cannula 16 were to project into this conical cavity so as to form an inward projecting lip, then it would be possible for air bubbles to become entrapped around the projecting lip. Additionally, the conical portion 30 serves to guide the inner cannula 12 so that the inner cannula 12 can be easily inserted inside the outer cannula 16. This guiding function is inhibited if there is a projecting lip of the outer cannula 16 extending into the conical section 30 is such that an inner cannula 12 would be inadvertently poked through the conical section 30 if the inner cannula 12 was directed against the conical section 30 by the projecting end of the outer cannula 16.

The widest portion of the conical portion 30 of support structure 28 ends at a cylindrical portion 32 which is molded integrally with the conical portion 30. The cyclindrical portion 32 has internal threads 34 molded into the silicon so that the cylindrical portion 32 of support structure 28 can be threaded or slid onto threads 36 (FIG. 1) which are on the tip of the surgical instrument 10 (FIG. 1).

There is a ring or continuous projection 38 on the inside of the cylindrical portion 32 adjacent the juncture with the conical portion 28. The continuous projection 38 has a "V" shape in cross-section and serves to provide a leak proof seal between the flexible support structure 28 and the tip of the surgical instrument 10 (FIG. 1). This seal between the support structure 28 and the tip of the surgical instrument 10 thus provides a fluid tight channel so that irrigation fluid can be forced through the slots 24, the conical portion 30, and the outer cannula 16 to exit through the irrigation apertures 18 in the outer cannula 16 without the need to pemanently deform the outer cannula 16.

For example, the lateral bending stiffness of the metal outer cannula 16 on the silicone support structure 28 as described above, is about 0.28 lbs./in. The lateral bending stiffness of a comparable all metal outer cannula 16 and support structure 28 is calculated as about 220 lbs./in., and essentially amounts to the cantilevered bending stiffness of the outer cannula 16 since the all metal support structure 28 acts as a rigid base. The bending stiffness of the all silicone cannulas and hub is about 0.025 to 0.035 lbs./in. Thus, the silicone-metal combination of this invention is a few hundred times more flexible (785 per above numbers) in bending than the comparable, all metal designs previously used. Phrased another way, the lateral bending stiffness of the silicone support structure 28 is about several thousand times more flexible in bending than is the metal outer cannula 16.

While the silicone support structure 28 is several thousand times more flexible than the outer cannula 16, it is believed a relative stiffness of one or two orders of magnitude (10 or 100) could suffice. The limiting criteria is believed to be that the flexibility of the silicone support structure 28 is sufficient to move or bend under the loads applied during surgery, and that the outer cannula 16 be strong enough to transfer those loads and to bend the support structure 28. Further, the outer cannula 16 must be strong enough not to collapse and restrict fluid flow if a suture is tightened around the outer cannula 16.

The axial stiffness of the metal-silicone combination is about 1.1 lbs./in. at a 5 gram load, and about 1.4 lbs./in. at a 20 gram load. The axial stiffness of an all metal structure is calculated at about 29,500 lbs./in., but the metal cannula 16 would buckle long before any substantial load was placed on it. Thus, the silicone-metal combination of this invention is about a few thousand times more flexible (2100 to 2700 per above numbers) in axial compression than the all metal prior art designs. Phrased another way, the axial stiffness of the support structure 28 is a few thousand times less, or more flexible, than the axial stiffness of the outer cannula 16.

While the silicone support structure 28 is a few thousand times more flexible in axial movement than the outer cannula 16, it is believed a relative stiffness of one or two orders of magnitude (10 or 100) could suffice. The limiting criteria is believed to be that the support structure 28 be sufficiently flexible to give or move under the axial loads experienced during use. Further, the outer cannula 16 must be sufficiently stiff in the axial direction to avoid buckling under the operational loads, and also be stiff enough to force the support structure 28 to move.

Figure 3:
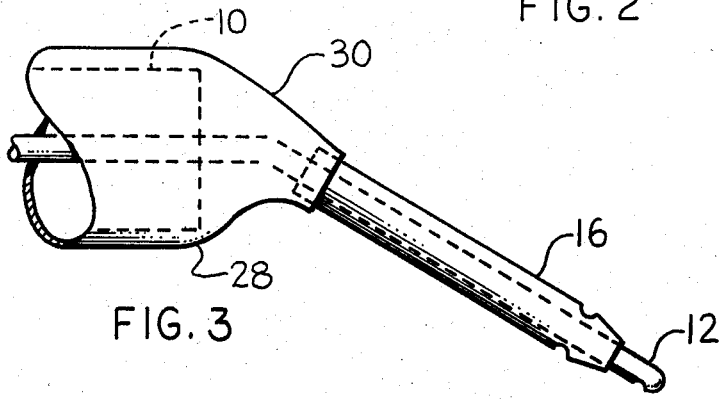
FIG. 3 is a perspective view showing the inner and outer cannulas of the invention in a bent position.

Referring to FIG. 3, the conical portion 30 of the flexible support structure 28 is sufficiently flexible with respect to the stiffness of the outer cannula 16 that the support structure 28 will bend and allow the outer cannula 16 to be rotated or skewed off axis without substantially deforming the cross-sectional shape of the outer cannula 16. Thus, the flexible support structure 28 bends to accommodate motion of the outer cannula 16.

This flexible motion is advantageous in that surgeons sometimes bend the inner cannula 12 and outer cannula 16 in order to facilitate access to various portions of the eye during surgery. The inner cannula 12 is relatively small in diameter and can be bent and re-bent fairly easily. Since the outer cannula 16 is flexibly mounted on the support structure 28, the support structure 28 flexes, rather than having the outer cannula 16 bend or buckle. The support structure 28 can allow repeated bending or repositioning of the outer cannula 16 without worry about the fatigue failure or fracture of the support structure 28 or the outer cannula 16. Thus there is no inhibition to rotational adjustment of the inner cannula 12 to adjust the spacing between the aspiration aperture 14 and the irrigation aperture 18, or to repeatedly bend the inner and outer cannula 12 and 16 respectively, in order to facilitate surgery.

Being made of a stiff material such as metal or hard plastic, the outer cannula 16 is significantly stiffer than the conical portion 30 of the support structure 28 which is made of silicon. The outer cannula 16 thus acts as though it were a rigid member mounted to a soft spring, the soft spring being the conical portion 30 of the flexible silicon support structure 28. When a radial force is applied to the outer cannula 16, all of the movement or rotation occurs primarily at the conical portion 30 of the support structure 28. This localized movement has the effect of localizing any restriction in the annular space between the inner cannula 12 and the outer cannula 16. The effect of this localized restriction is that any resistance to flow of the irrigation fluid is minimized since the restriction will be of a local nature rather than having the restriction extend along a substantial length of the outer cannula 16. Further, during bending or rotation of the inner cannula 12, the outer cannula 16 does not crimp or distort its cross-sectional area so as to appreciably decrease the irrigation efficiency of the outer cannula 16. Thus, a greater irrigation efficiency and higher irrigation flow rates are possible by this minimization of the restrictions to fluid flow.

This localized bending of the outer cannula 16 about the support structure 28 provides sufficient adjustment or bending capability for most of the surgeon's needs. Additional adjustments can be made, however, by bending the outer cannula 16 to the extent allowable before the material fractures.

The outer cannula 16 has a relatively short length which provides a minimum amount of resistance to the flow of the irrigation fluid through the tip of the surgical instrument 10 and through the outer cannula 16 and the irrigation apertures 18 (FIG. 1). This minimal resistance to fluid flow provides a very efficient irrigation system which can operate at greater flow rates than were possible if the length outer cannula 16 were increased.

Referring to FIGS. 1 and 3, the flexibility of the support structure 28 also cooperates with the gap between the external end 26 (FIG. 1) of outer cannula 16, and the adjacent portion of inner cannula 12, to minimize damage to the eye during surgery. While the gap or space between the external end 26 of outer cannula 16 is small, the gap allows the outer cannula 16 to float or more slightly when rubbed against eye tissues. While the amount of movement may seem small, this ability to flexibly yield against pressure is important to minimize damage to the fragile tissues in the eye. Since the outer cannula 16 is rigid relative to the support structure, a lever effect is obtained which allows a small force to move or pivot the outer cannula 16 (acting as a lever) about its support structure 28. This lever effect reduces the amount of force which the fragile eye tissue must exert in order to move the outer cannula 16. The flexible support structure 28 allows this motion which cannot be obtained in structures made entirely of metal.

The use of a metal or smooth finish hard plastic on the outer cannula 16 provides a further reduction to the risk of damaging the fragile eye tissue. The metal or smooth hard plastic will slide along the eye tissue without abrading or tearing as is possible with the rougher finish found on cannulas which are made entirely of silicone rubber.

The flexibility of the conical portion 30 of the support structure 28 also provides for a flexible support along the length of the cylindrical axis of the outer cannula 16. The silicon of the support structure 28 is significantly more flexible than either a hard plastic or metal. Thus the support structure 28 provides the outer cannula 16 with an axial give or flexibility so as to minimize any damage that might be caused when the external end 26 contacts a portion of the sclera or other portions of the eye during insertion into the eye for surgery. At the same time, the outer cannula 16 is still strong enough to avoid the axial buckling problems which occur when the outer cannula 16 is made of silicone.

I claim:

1. A device for use on a surgical irrigation/aspiration instrument, comprising:
   a cannula having first and second ends, said cannula having a first aperture adjacent said first end for communicating with a portion of the body, and having a second aperture adjacent said second end for communicating with said surgical instrument; and a flexible support connecting said second aperture of said cannula to said surgical instrument so as to provide a fluid tight connection, said flexible support forming a flexible joint adjacent said second cannula, said flexible support being made of a more flexible material than said cannula so as to allow said cannula to rotate about said support without the need to deform said cannula to cause said rotation.

2. A device as defined in claim 1, wherein said cannula comprises an irrigation cannula for transmitting fluid from said surgical instrument to said body portion in order to irrigate said body portion.

3. A device as defined in claims 1 or 2 wherein said cannula is made of metal while said flexible support is made of a silicon compound.

4. A device for use on a surgical irrigation/aspiration instrument comprising:

cannula means for communicating with a portion of the body so as to carry fluids between said body and said surgical instrument; and flexible support means which is made of a more flexible material than said cannula, for connecting said cannula means to said surgical instrument so as to allow movement of said cannula means about said support means while providing a leak proof coupling to help carry fluids between said body and said surgical instrument, said flexible support means forming a flexible joint adjacent one end of said cannula.

5. A device as defined in claim 4, wherein said cannula comprise an irrigation cannula for transmitting fluid from said surgical instrument to said body portion in order to irrigate said body portion.

6. A device as defined in claims 4 or 5 wherein said cannula is made of metal while said flexible support is made of rubber.

7. A device as defined in claims 1 or 4 wherein said flexible support is approximately a few hundred times more flexible in lateral bending than said cannula.

8. A device as defined in claims 1 or 4 wherein said flexible support is approximately a few thousand times more flexible in axial compression than said cannula.

9. An intraocular surgical instrument for simultaneous irrigation and aspiration, comprising:

an inner cannula for transporting fluids between said surgical instrument and an eye;

an outer cannula, coaxial with, and substantially surrounding said inner cannula so as to form a generally annular space between said inner and outer cannulas, said outer cannula transporting fluids between said surgical instrument and said eye;

a flexible support connecting said outer cannula to said surgical instrument so as to provide a leak proof connection to allow said outer cannula to transport fluids between said eye and said surgical instrument, said flexible support being flexible relative to the stiffness of said cannula so as to allow said cannula to rotate about said flexible support without permanently deforming said outer cannula;

a suction device connected to said surgical instrument and communicating with one of said inner and outer cannulas so as to create a suction to transport fluids from said eye to said surgical instrument;

an irrigation device connected to said surgical instrument and communicating with the other of said inner and outer cannulas so as to provide fluid to said eye to irrigate said eye.

10. A surgical instrument as defined in claim 9 wherein said outer cannula communicates with said irrigation device, and wherein said inner cannula communicates with said suction device.

11. A surgical instrument as defined in claim 9 or 10 wherein said outer cannula is made of metal and said inner cannula is made of silicon rubber.

12. A device as defined in claim 9 wherein said flexible support is approximately a few hundred times more flexible in lateral bending that said cannula.

13. A device as defined in claim 9 wherein said flexible support is approximately a few thousand times more flexible in axial compression than said cannula.

14. A device as defined in claim 1 or 4, wherein said flexible support is about 100 times as flexible as said cannula in lateral bending.

15. A device as defined in claims 1 or 4 wherein said flexible support is about 100 times as flexible as said cannula along the axial direction of said cannula.

* * * * *